United States Patent [19]

Gfrerer

[11] 4,394,193
[45] Jul. 19, 1983

[54] METHOD AND DEVICE FOR THE CONTINUOUS, CONTACTLESS MONITORING OF THE STRUCTURE STATE OF COLD STRIP

[75] Inventor: Manfred Gfrerer, Erlangen, Fed. Rep. of Germany

[73] Assignee: Siemens Aktiengesellschaft, Munich, Fed. Rep. of Germany

[21] Appl. No.: 254,613

[22] Filed: Apr. 16, 1981

[30] Foreign Application Priority Data

Apr. 24, 1980 [DE] Fed. Rep. of Germany ....... 3015894

[51] Int. Cl.³ ............................................... C21D 1/54
[52] U.S. Cl. .................................................. 148/129
[58] Field of Search ................. 148/129; 324/224, 222

[56] References Cited

U.S. PATENT DOCUMENTS

| | | | |
|---|---|---|---|
| 2,059,054 | 10/1936 | Stargardter | 148/129 |
| 2,211,017 | 8/1940 | Leifer et al. | 324/224 |
| 2,534,420 | 12/1950 | Delaney | 324/222 |
| 2,828,467 | 3/1958 | Stauffer | 324/222 |
| 3,130,363 | 4/1964 | Camp et al. | 148/129 |
| 3,281,678 | 10/1966 | Cilyo | 324/222 |
| 3,723,859 | 3/1973 | Leonard | 324/222 |

*Primary Examiner*—Peter K. Skiff
*Attorney, Agent, or Firm*—Kenyon & Kenyon

[57] ABSTRACT

Internal structure of a metal strip is monitored by applying cyclically varying magnetic flux to the strip and sensing the flux induced in the strip. Signals corresponding to the magnetic field intensity of the applied cyclically varying field and to the resulting induced flux indicate the loss of energy due to the internal structure of the strip. Making a similar determination by similar monitoring apparatus following annealing of the strip allows the effect of the annealing to be determined. The signals from the two monitoring apparatus can be used to generate a comparison signal to control the operation of the annealing treatment apparatus.

5 Claims, 4 Drawing Figures

METHOD AND DEVICE FOR THE CONTINUOUS, CONTACTLESS MONITORING OF THE STRUCTURE STATE OF COLD STRIP

BACKGROUND OF THE INVENTION

This invention relates to a method and apparatus for continuously monitoring the internal structure of metal strip subjected to an annealing treatment. In particular, it relates to the continuous, contactless monitoring of the grain structure of cold metal strip to determine the effect of annealing. The monitoring is done by means of a measuring arrangement consisting of at least one magnetic flux-producing device and a measuring sensor immediately associated therewith to determine energy loss.

Continuous, contactless monitoring of the internal structure of an elongated magnetizable material, preferably after heat treatment, is described in DE-AS Nos. 20 50 827 and 20 65 826. In order to judge the internal structure, an apparent remanence is used as the measuring variable which represents a measure of the coercivity. The coercivity reaches a minimum if the strip is completely recrystallized by an annealing treatment. The measuring arrangement comprises a magnetizing device that includes cylindrical permanent magents and a measuring sensor separated by a certain distance from the magnetizing device and containing a Hall probe. The strip travels through a measuring path past the magnetizing device and the measuring sensor, and the Hall voltage generated by the measuring sensor is evaluated and recorded as a measure of the apparent remanence.

One disadvantage of that method is that the measuring apparatus is sensitive to changes in the distance between the strip, the measuring device, and the measuring sensor as well as to shock and vibration, and is influenced by remanent external fields. The prior art methods are also limited to measuring strips of ferromagnetic material.

OBJECTS AND SUMMARY OF THE INVENTION

It is an object of the present invention to monitor the internal structure of conductive strips, whether they are ferromagnetic or nonmagnetic material.

Another object is to accomplish the measurement independently of changes in the position in the strip passing through the measuring apparatus.

According to the present invention, monitoring the internal structure of conductive strips before and after, or even during, an annealing treatment is accomplished by determining the hysteresis loop areas of the strip at selected points, which may differ in time or location or both, and comparing such areas with each other. The difference between them is evaluated as a measure of the internal structure of the strip and, particularly, of the degree of recrystallization due to the annealing treatment.

The measuring apparatus, which is also an aspect of this invention, includes an electromagnet that comprises an iron core with an air gap and, on the core on one side of the gap, an exciter coil that can be connected to an a-c source. A measuring sensor in the form of a measuring coil or Hall probe is located on the core on the other side of the gap. Because of the possibility of magnetizing the strip via the exciter coil in the range of maximum induction, a high measuring sensitivity can be achieved. Since the flux intensity varies cyclically in accordance with the a-c, eddy current losses in the strip are also taken into consideration, so that both ferromagnetic and nonmagnetic materials can be monitored. Because the exciter coil and the measuring sensor are arranged on a common iron core, the induction is measured simultaneously with generation of the magnetic field by the coil, and information loss is minimized. Any residual magnetic fields in the vicinity, which could falsify the measurement, are eliminated through the use of a cyclically varying magnetic field.

DETAILED DESCRIPTION OF THE INVENTION

Figures 1, 2:
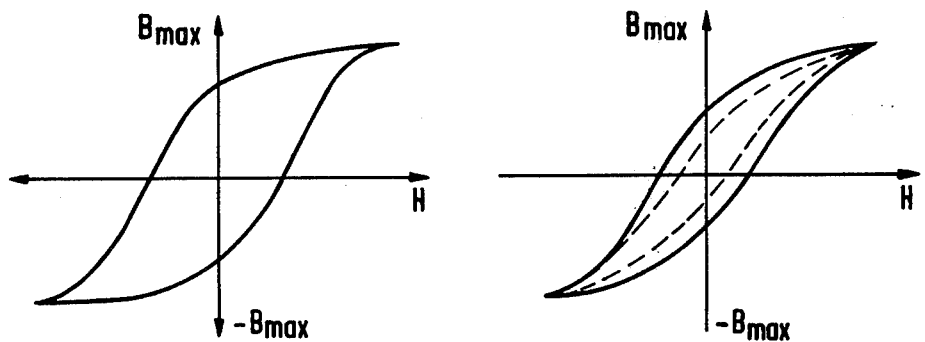
FIG. 1 shows a typical hysteresis curve for magnetic material.
FIG. 2 shows two hysteresis curves of different area for the same material, representing different annealing conditions.

As shown in FIGS. 1 and 2, the hysteresis loop area of a cold-deformed material containing ferromagnetic components is larger (FIG. 1) than the area of the hysteresis loop of the same material annealed to recrystallization (FIG. 2). By measuring the magnetic hysteresis, it is therefore possible to draw conclusions as to the internal structure, especially the state of recrystallization, of a metal sample, for instance, a strip of sheet metal.

Figure 3:
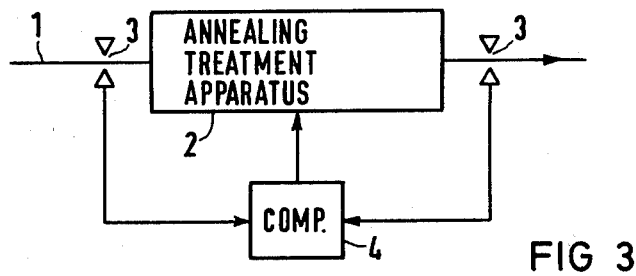
FIG. 3 is a block diagram of annealing apparatus and monitoring and control apparatus attached thereto.

According to the schematic presentation in FIG. 3, a metal strip 1 travels continuously through annealing treatment apparatus 2 from left to right. On the entrance side and on the exit side of the annealing treatment apparatus are similar measuring devices 3, each of which is connected to feed its measured data to a computer 4. The data comprise, essentially, measurements of areas of the hysteresis loops of the strip 1 at the two measuring devices 3. The area of a hysteresis loop is a measure of energy lost in applying a cyclically varying magnetic field to ferromagnetic material. Applying the same cyclically varying magnetic field to conductive material that is nonmagnetic produces eddy current losses measurable on the same apparatus 3. The computer compares the measured values with each other and controls, as a function of the difference resulting from the comparison, the annealing parameters, such as the annealing temperature of the dwelling time of the strip in the annealing zone or both in such a manner that the desired internal structure in the strip emerging from the annealing apparatus 2 is obtained.

Figure 4:
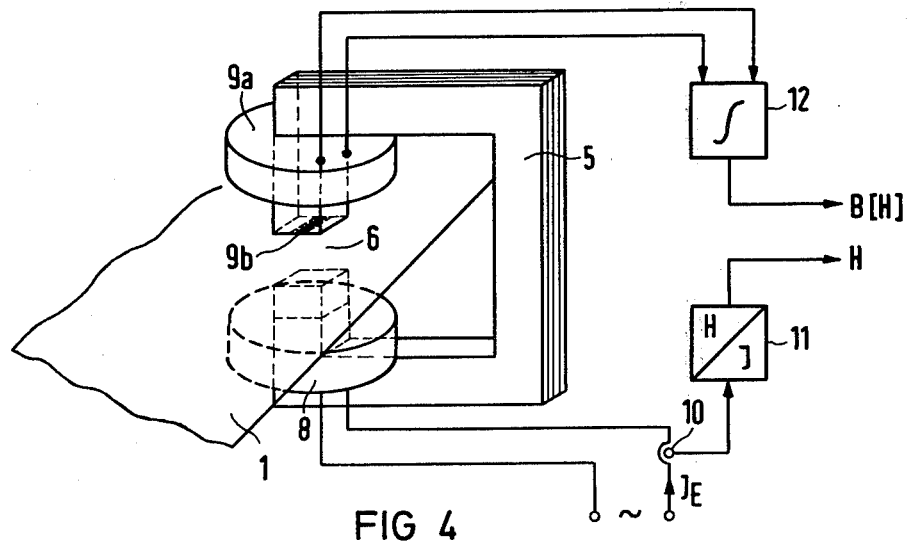
FIG. 4 is a schematic representation of measuring apparatus in accordance with this invention.

In FIG. 4, part of the measuring apparatus is shown in perspective view. An iron core 5 is constructed in the manner of a C-shaped transformer core provided with an air gap 6 through which a strip 1 that is to be monitored travels. An exciter coil 8 is mounted on one end section of the iron core adjacent one side of the air gap and is provided with terminals to be connected to an a-c source. The coil 8 and a-c source are preferably capable of generating sufficient magnetic field intensity to furnish the maximum induction in the strip 1. On the other end section of the iron core is a coil 9a arranged as a measuring sensor. The drawing also shows another form of sensor, such as a Hall probe or a field plate 9b, arranged on the face of this end section to the core 5. It is not necessary to use both types of sensors 9a and 9b; either will do.

Current to excite the coil 8 flows through the primary of a current transformer 10, the secondary side of which provides proportional current to a device 11. This device transforms the current proportional to the exciter current into a quantity proportional to the magnetic field strength H.

The voltage induced by cyclically varying flux that reaches the measuring sensor 9 is converted via a converter 12, for example, an integrator, into a measuring variable proportional to the magnetic induction B in the strip 1. The hysteresis loop area is calculated from the quantities B and H. The area of the hysteresis loop in FIG. 1 measured on the entrance side of the annealing apparatus 2 in FIG. 3 is compared with the hysteresis loop area in FIG. 2 as measured on the exit side of the annealing treatment apparatus. The latter area is a measure of the quality of the recrystallization accomplished by the annealing treatment apparatus, and if this area is too large, as indicated by the loop in solid lines in FIG. 2, it indicates that the strip 1 has been insufficiently annealed. As a result, the computer 4 in FIG. 3 causes the heat applied to the strip 1 to increase or the velocity at which the strip passes through the apparatus to decrease until a hysteresis loop indicated in dotted lines in FIG. 2 is measured at the output side of the annealing treatment apparatus 2 in FIG. 3.

It may be that only a limited recrystallization is necessary. In that case, the hysteresis loop in dotted lines in FIG. 2 may be unnecessarily small, so that the computer 4 must decrease the heat or increase the strip velocity, or both, in the annealing treatment apparatus 2 until a hysteresis loop area shown in solid lines in FIG. 2 is measured.

Placing both the exciter coil 8 and the sensor device 9 on the same core 5, and determining the sensor output at the same time the strip 1 is subjected to flux from the coil 8 eliminates any discrepancy due to movement of the strip between the time the flux is produced and the time the sensing occurs. In addition, as long as the strip 1 passes through the gap 6, it makes relatively little difference whether the strip moves slightly closer to the coil 8 or to the sensor 9, whereas in the prior art devices, it is essential that the magnetizing components and the sensing components maintain a fixed relationship to the strip.

The measurement of losses has been described primarily in terms of measurement of the size of the hysteresis loop area. More specifically, what is actually computed by the device 11 and the converter, or integrator, 12 are signals that correspond to information that would be used in drawing a hysteresis loop so that its area could be measured. The losses are the important factors, not the areas per se, whether the losses are due to the nonlinear magnetization characteristics of iron or to the dissipation of heat due to eddy currents. The calculation of either of these losses requires that the intensity of the applied cyclically varying flux be measured and the intensity of induced flux also be measured and that a functional relationship be established, as by the integrator 12. Since both types of losses are due to magnetic fields, they have been referred to herein as hysteresis losses.

What is claimed is:

1. A method for continuous monitoring of the internal structure of a metal strip subjected to an annealing treatment, said method comprising the steps of:
    inducing a first magnetic flux of cyclically varying intensity in the strip at one point in the annealing treatment;
    simultaneously measuring the intensity of the first flux modified by said strip;
    forming a first predetermined functional relationship between the measured intensity and the induced intensity to determine energy lost due to variation of the intensity of the first flux;
    inducing a second magnetic flux of cyclically varying intensity in said strip at a later point in the annealing treatment;
    simultaneously measuring the intensity of the second flux modified by said strip;
    forming a second predetermined functional relationship between the measured intensity and the induced intensity of the second flux to determine energy lost due to variation of the intensity of the second flux;
    comparing the energy lost due to variation of the first flux to energy lost due to variation of the second flux to obtain a measure of the change of internal structure of the metal strip between the first and second points, and
    controlling the annealing process as a measure of said change.

2. The method according to claim 1 in which the first and second points are separated by time.

3. The method according to claim 1 in which the first and second points are separated by distance.

4. The method according to claim 1 in which the annealing treatment includes moving the strip through a controlled temperature zone at a controlled velocity, said step of controlling the annealing comprising controlling the temperature in the zone in response to the comparison of the energy lost due to variation of the first flux to energy lost due to variation of the second flux.

5. A method for continuously monitoring the internal structure of a conductive strip subjected to an annealing treatment, said method comprising the steps of:
    measuring a first hysteresis loop area on a region of the strip prior to the entry of that area into the annealing treatment, and measuring a second hysteresis loop area on a region of the strip that has emerged from the annealing treatment;
    comparing the measured hysteresis loop areas as a measure for determining the degree of recrystallization; and
    controlling the annealing treatment as a function of the difference of the hysteresis areas at the two points.

* * * * *